United States Patent
Reiz

(10) Patent No.: US 9,816,943 B2
(45) Date of Patent: Nov. 14, 2017

(54) CONTACTLESS EXAMINATION OF A BUTT WELD

(71) Applicant: Georg Fischer Rohrleitungssysteme AG, Schaffhausen (CH)

(72) Inventor: Robert Reiz, Wutoeschingen (DE)

(73) Assignee: GEORG FISCHER ROHRLEITUNGSSYSTEME AG, Schaffhausen (CH)

( * ) Notice: Subject to any disclaimer, the term of this patent is extended or adjusted under 35 U.S.C. 154(b) by 0 days.

(21) Appl. No.: 14/748,419

(22) Filed: Jun. 24, 2015

(65) Prior Publication Data

US 2016/0003751 A1   Jan. 7, 2016

(30) Foreign Application Priority Data

Jul. 4, 2014  (EP) ...................................... 14175829

(51) Int. Cl.
  *G01N 21/952* (2006.01)
  *B29C 65/82* (2006.01)
  *B29C 65/00* (2006.01)
  *B29C 65/02* (2006.01)
  *G01B 11/24* (2006.01)

(52) U.S. Cl.
  CPC ........... *G01N 21/952* (2013.01); *B29C 65/02* (2013.01); *B29C 65/8253* (2013.01); *B29C 66/1142* (2013.01); *B29C 66/5221* (2013.01); *B29C 66/974* (2013.01); *G01B 11/24* (2013.01); *G01N 2201/062* (2013.01)

(58) Field of Classification Search
  CPC ........... G01N 21/952; G01N 2201/062; G01B 11/24; B29C 65/8253; B29C 66/5221; B29C 65/02

USPC ........ 356/445–446; 73/595, 598, 588, 865.8, 73/622, 624, 625; 219/121.63, 121.64, 219/121.83; 156/64, 304.1, 304.2
  See application file for complete search history.

(56) References Cited

U.S. PATENT DOCUMENTS

| | | | | |
|---|---|---|---|---|
| 4,160,386 A | * | 7/1979 | Jackson | G01N 29/223 367/117 |
| 4,375,165 A | * | 3/1983 | de Sterke | G01N 29/265 73/622 |
| 4,429,211 A | * | 1/1984 | Carstens | B23K 26/04 219/121.63 |
| 4,481,824 A | * | 11/1984 | Fujimoto | G01N 29/11 73/599 |
| 4,734,766 A | * | 3/1988 | Shiozumi | G01B 11/024 356/608 |
| 5,263,362 A | * | 11/1993 | Karl | G01M 3/2884 73/40 |

(Continued)

FOREIGN PATENT DOCUMENTS

| | | |
|---|---|---|
| DE | 102012007563 B3 | 5/2013 |
| DE | 202014100284 U1 | 2/2014 |

(Continued)

*Primary Examiner* — Sang Nguyen
(74) *Attorney, Agent, or Firm* — Leydig, Voit & Mayer, Ltd.

(57) ABSTRACT

A device for the contactless examination of a butt weld of plastic pipes and fittings is provided. The device includes a carrier device, an illumination unit, and at least one sensor for monitoring the pipe ends or fitting ends to be welded and the weld seam, wherein the sensor is an electronic light-sensitive sensor.

13 Claims, 6 Drawing Sheets

(56) References Cited

U.S. PATENT DOCUMENTS

| | | | | |
|---|---|---|---|---|
| 5,347,101 | A * | 9/1994 | Brennan | B23K 9/0286 219/124.34 |
| 5,777,229 | A * | 7/1998 | Geier | G01N 29/2412 228/104 |
| 5,837,966 | A * | 11/1998 | Timmons, Jr. | B23K 9/0286 219/124.34 |
| 5,948,190 | A * | 9/1999 | Haug | B29C 65/20 156/304.1 |
| 6,045,640 | A * | 4/2000 | Wermelinger | B29C 65/20 156/304.6 |
| 6,084,203 | A * | 7/2000 | Bonigen | B23K 26/04 219/121.63 |
| 6,084,223 | A * | 7/2000 | Dietz | B23K 26/032 219/121.64 |
| 2002/0084260 | A1 | 7/2002 | Kubota et al. | |
| 2004/0011775 | A1* | 1/2004 | Hackl | B23K 9/1087 219/124.34 |
| 2004/0179206 | A1 | 9/2004 | Tassakos et al. | |
| 2004/0244509 | A1* | 12/2004 | Savitski | B29C 66/91921 73/865.8 |
| 2005/0223807 | A1* | 10/2005 | Bardoux | B23K 31/12 73/598 |
| 2007/0119829 | A1 | 5/2007 | Vietz et al. | |
| 2008/0237308 | A1* | 10/2008 | Den Boer | B23K 20/028 228/164 |
| 2009/0114021 | A1* | 5/2009 | den Boer | G01N 29/07 73/596 |
| 2009/0279096 | A1* | 11/2009 | Lim | G01N 21/55 356/446 |
| 2010/0314362 | A1 | 12/2010 | Albrecht | |
| 2013/0068384 | A1* | 3/2013 | Liu | C03B 23/203 156/272.8 |
| 2015/0060436 | A1 | 3/2015 | Kocks et al. | |

FOREIGN PATENT DOCUMENTS

| | | |
|---|---|---|
| JP | 2000289115 A * | 10/2000 |
| WO | WO 2014063153 A1 | 4/2014 |

* cited by examiner

CONTACTLESS EXAMINATION OF A BUTT WELD

CROSS-REFERENCE TO RELATED APPLICATION

This application claims priority from European Patent Application No. 14 175 829.2, filed Jul. 4, 2014, which is incorporated by reference herein in its entirety.

FIELD

The invention relates generally to examination of welds, an in particular to a device and a method for the contactless examination of a butt weld of plastic pipes and fittings.

BACKGROUND

An examination of a butt weld is used to ensure the quality of the welding. It does not matter which method is used to butt weld the pipes or fittings, whether it is by means of contactless IR welding methods, by means of the classical butt welding method by touching a hot mirror, or another method, in accordance with the pipes or fittings to be welded, i.e., the dimensions thereof, the plastic thereof, the welding technology which is applied, etc., a weld seam is to have a specific shape or size, which can be visually examined. Guidelines or standards exist corresponding thereto, which precisely define how a seam should appear or how the permissible dimensions should be in relation to the pipe or fitting and welding properties, so that they meet the requirements. Up to this point, a manual visual judgment has usually been carried out by a responsible technician, who compares and judges the resulting weld seam on the basis of the standards and guidelines known thereto.

It is disadvantageous in this case that judgments by a technician are very time-consuming and therefore very costly. In addition, such a judgment is also not consistent, since human subjectivity plays a role and the examination is not always performed by the same technician.

JP 2000289115 A discloses an examination of a weld of plastic pipes by means of an ultrasound sensor, whereby a statement with respect to the melting of the pipe wall in the interior, which is not visible, can also be achieved. However, the high expenditure of this method is disadvantageous in this examination since such an examination is very time-consuming, because, inter alia, the weld must be completely cold before such an examination can take place, which is not ideal for the installation of a pipeline having diverse weld seams.

SUMMARY

A device for the contactless examination of a butt weld of plastic pipes and fittings is provided. The device includes a carrier device, an illumination unit, and at least one sensor for monitoring the pipe ends or fitting ends to be welded and the weld seam, wherein the sensor is an electronic light-sensitive sensor.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
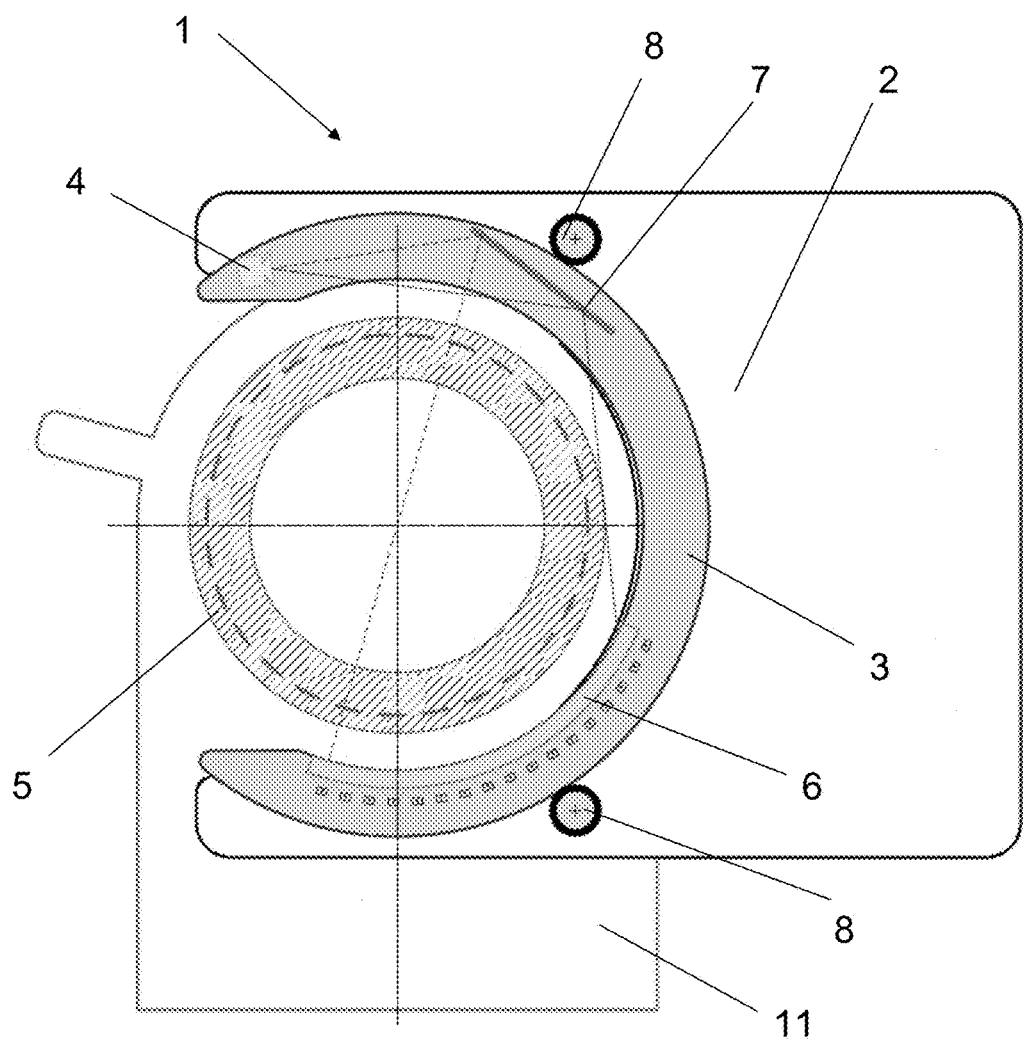
FIG. 1 shows a schematic view of a device according to an embodiment of the invention.

It is an object of an embodiment of the invention to propose a device and a method linked thereto, which enable a non-destructive, or contactless, consistent quality examination of a weld in the case of butt-welded plastic pipes, without an economic disadvantage resulting due to a higher expenditure of time.

This object is achieved according to an embodiment of the invention in that the sensor for the contactless examination of the weld is an electronic light-sensitive sensor, preferably a digital camera, and the contactless examination is carried out by means of an electronic light-sensitive sensor, preferably a digital camera.

A device according to an embodiment of the invention contains a carrier device, wherein it is designed and embodied in accordance with the application of the device or the field of use thereof, whereby the device according to an embodiment of the invention can be produced as an autonomous examination device or can be implemented as a module which can be retrofitted for an existing butt welding machine.

The device according to an embodiment of the invention can also be implemented such that it is fixedly integrated on a butt welding machine.

In accordance with the application, an operating unit can also be provided or can be omitted in different embodiments of the invention, since possibly the operating unit of the welding machine can be used.

In addition, according to an embodiment of the invention, the device has an illumination unit to illuminate the weld seam or the pipe ends during the examination or the recording by means of the sensor, so that the contours of the weld seam or weld bead and also the pipe ends before the welding process are clearly recognizable.

The sensor or the digital camera makes recordings of the welding or the weld seam and also the pipe ends to be welded before the welding. A CCD sensor, CMOS sensor, or another electronic light-sensitive sensor known from the prior art, which has a compact construction, can be installed as an electronic light-sensitive sensor. Of course, a digital camera can also be used, since these usually contain such a sensor. In addition, the digital cameras known from the prior art are so small that they can be used without problems for the present invention. The recordings of the weld seam or the pipe ends can run as a film or continuously or individual image recordings can also be taken, the individually taken image recordings can be individually selected during an examination of a weld seam. The sensor or the digital camera is arranged so it is movable or moving on the sensor carrier or can be aligned accordingly, if necessary.

In an embodiment, the device according to an embodiment of the invention has a sensor carrier. The sensor is preferably arranged on the sensor carrier and the sensor carrier is in turn arranged on the carrier device.

The sensor carrier can be arranged so it is movable or rotatable on the carrier device, and the sensor carrier is thus rotatable on the carrier device around an axis, wherein the carrier device forms a fixed base.

In an embodiment, the sensor carrier may be rotated by 360° around the pipe or the weld. The sensor, which is arranged on the sensor carrier, thus can also move around the pipe and can record or examine the complete weld seam or the pipe ends before the welding.

The sensor carrier can have a C shape. This enables simple positioning of the sensor carrier around the pipe circumference in that the C-shaped sensor carrier is moved over the pipe circumference, since the opening of the C shape is sufficiently large that the largest pipe diameter which can be examined using the device according to an embodiment of the invention can be pushed through the opening of the C shape or the sensor carrier can be pushed over the pipe. The pipe ends to be welded are then concentrically enclosed by the sensor carrier. This shape of the sensor carrier enables the sensor carrier and therefore also the sensor to circle the pipe or the weld seam by 360°.

The sensor can be arranged on the sensor carrier such that the viewing angle or the field of vision of the sensor enable it to capture and examine different pipe dimensions using the same device according to an embodiment of the invention, without having to perform a modification or an adjustment of the device. As already mentioned, the sensor is preferably arranged on the sensor carrier so it is movable, preferably pivotable, whereby a fine adjustment of the sensor is possible.

The sensor can be aligned tangentially on the pipe circumference, in a proven manner such that, as already mentioned above, as many dimensions of the pipe as possible can be captured using one device or one sensor setting.

The illumination unit can also be arranged at a defined distance to the sensor on the sensor carrier and can move around the pipe or the weld seam. In an embodiment, the illumination unit is arranged on the sensor carrier such that it forms a backlight for the sensor.

In an embodiment in which the illumination unit is used as a backlight, the different pipe diameters for which the device is applicable can also be covered here. That is to say that it forms a backlight for the sensor in the case of the smallest and also the largest diameter which can be examined on the device. The illumination unit can therefore be implemented as a light screen, i.e., the illumination unit extends over a specific range. The illumination unit arranged on the sensor carrier, wherein the sensor carrier preferably has a C shape, extends on the C shape over a specific length, so that any pipe diameter can accordingly be illuminated well by the light screen. The light screen can especially be turned on or off in sections, so that in each case only the section of the light screen is illuminated which forms the optimum backlight for the sensor. For example, LEDs can be used for the illumination unit, which are arranged along the sensor carrier such that they form a light screen and can be turned on or off in sections.

A device according to an embodiment of the invention has a mirror, wherein the mirror is preferably arranged on the sensor carrier. The mirror can be arranged so it is movable on the sensor carrier, this enables a fine alignment of the mirror. The mirror is used to enlarge the optical path between the sensor and the weld seam to be recorded. In addition, the viewing angle between the sensor and the weld seam is varied. In this embodiment of the device according to an embodiment of the invention, the sensor is not oriented directly tangentially onto the pipe circumference, rather it is oriented indirectly tangentially onto the pipeline circumference via a mirror. It has been shown to be advantageous that the mirror and/or the sensor are arranged so they are movable on the sensor carrier, so that a fine adjustment can be performed. The illumination unit is arranged such that a backlight is formed, i.e., the backlight radiates tangentially on the pipe circumference and directly into the mirror, which redirects the light to the sensor. The distance between backlight and weld seam, which is tangentially illuminated, thus remains equal as without mirror, but the distance between sensor or the digital camera and the weld seam or the pipe circumference at the position at which the recording is made is enlarged in contrast to the arrangement without mirror. The perceived width of the backlight is thus enlarged and enables an illumination of the entire weld seam or a coverage of the entire width of the weld bead by means of the backlight, whereby the weld seam is illuminated completely from the rear, presuming that the distance of the backlight to the weld seam remains constant. This in turn is used for clear recognition and capture of the contour of the weld seam or the weld bead during the recordings.

A further embodiment of the device according to an embodiment of the invention is that the illumination unit is arranged as an incident light on the sensor carrier and also the sensor or the digital camera is oriented perpendicularly or approximately perpendicularly to the external diameter of the pipeline or the weld seam. The sensor is therefore aligned approximately perpendicularly, so that a reflection of the illumination unit on the weld seam can be avoided, whereby the resulting recordings are clearer. The surface composition of the position to be examined can be ascertained by this arrangement of the sensor and the illumination unit. Wherein the embodiment of the tangential or indirectly tangential sensor with the backlight and the sensor oriented perpendicularly to the circumference with the incident light can be arranged both in combination and also separately on the sensor carrier.

The method according to an embodiment of the invention for the contactless examination of a butt weld of plastic pipes includes the following steps: The pipe ends to be welded are preferably fastened by means of pipe clamps on the butt welding machine, so that the two end sides to be welded are opposite to one another. The pipe ends are subsequently planed so that clean and planar end sides are provided and are thus prepared for the welding.

The pipe ends to be welded can already be examined in a contactless manner as soon as they are fastened and planed in the pipe clamps on the butt welding machine, for example. The external diameter of the pipe ends to be welded and also their ovality and their mutual offset to one another can be examined and corrected if necessary, for example. Or at least the pipes or the flaws thereof can thus be recognized early and discarded or replaced. In addition, the possibility exists of already recognizing at this point in time by means of the method according to an embodiment of the invention whether the surface of the pipe ends to be welded is sufficiently clean and smooth. Further examinations and recognitions such as material recognition, colour recognition, parallelism of the pipes, etc. are also conceivable by way of the method according to an embodiment of the invention.

Subsequently, the welding can be carried out, wherein the previously performed contactless examination of the pipe ends does not represent a requirement in the method for examining the weld seam.

Any method known from the prior art can be applied for the welding, for example, IR welding, butt welding by means of touching on the hot mirror, etc.

Subsequently, the contactless examination of the weld seam or the weld bead is performed. An advantage, in this case, is that the examination, since it is contactless, can already be performed during the cooling procedure, whereby an additional time expenditure for a subsequent examination after the cooling can be avoided, which enables rapid and expeditious laying of a pipeline. The contactless examination is carried out by means of an electronic light-sensitive sensor, preferably a digital camera, both for the examination of the weld seam and also the optional procedure of examining the pipe ends. Of course, the possible embodiments, as described above with reference to the device, are also applicable to the method. The sensor captures the contour of the weld seam or weld bead, such as width, shape, etc., whereby the cross-sectional area of the weld seam can also be ascertained. If an examination of the pipe ends has also taken place before the welding, the contour of the pipe ends and the further properties thereof are also captured and possibly analyzed by means of a controller. The sensor captures the data continuously or as a film, or also individual recordings along the circumference are possible. For this purpose, the sensor rotates around the pipe circumference or around the weld seam, whereby the entire seam is captured and examined without changing the pipes in the location thereof.

In order that the ascertained recordings result in sharp and clear contours, the weld seam can be illuminated, preferably by a backlight on the tangentially or indirectly tangentially oriented sensor, which clearly emphasizes the contours of the weld seam or the weld bead or the pipe ends and makes them well recognizable.

These data ascertained by the sensor are then compared to and checked with the data stored in the controller, which are based on standards and/or guidelines, which specify which dimension and shape a weld seam must have for specific requirements using the welded plastic pipes so that they meet the requirements. It can then be stated on the basis of this analysis whether the weld seam corresponds to the requirements. In addition, it can also be ascertained by the sensor, which is oriented perpendicularly onto the pipe circumference or the weld seam and is illuminated with incident light, whether irritations or contaminants are present on the surface of the weld seam or weld bead, which could possibly also result in weakening of the weld. All of these analyses can be performed by means of the controller on the basis of the established boundary conditions for the weld seam, which are generally defined by standards. Or the data (dimension and area specifications) are provided to the user to be used as a decision aid.

The data captured by the device can also be stored to document the welding process or the welding result and/or to enable a subsequent judgment of the weld seam.

Figure 3:
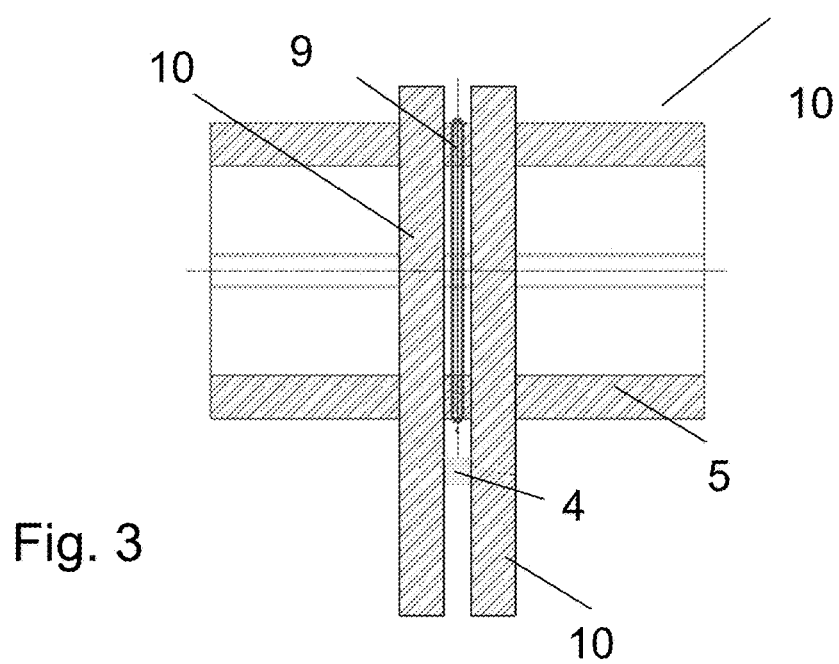
FIG. 3 shows a schematic longitudinal section through the pipe clamp and the welded pipe ends.

FIG. 1 shows a schematic illustration of a device 1 according to an embodiment of the invention, wherein the device 1 for contactless examination of a butt weld contains a carrier device 2. The device 1 illustrated in FIG. 1 is solely schematic, because of which the carrier device 2 is also only illustrated as a rectangular plate 2. Of course, the carrier device 2 can have a different shape, and also further features, for example, a display or switches. In addition, it is also to be designed in accordance with the application of the device 1 so that, for example, it is implemented so that it is adaptable to a butt welding machine and, for example, can be placed in the butt welding machine by pivoting in between the pipe clamps 10 in FIG. 3, similarly to a hot mirror. Of course, other adaptations to a welding machine are also conceivable. By way of a modular construction of the device 1 according to an embodiment of the invention, it is usable as desired and is also suitable for retrofitting. The device 1 can also be implemented as autonomous and can have a separate controller and display. A sensor carrier 3 is arranged on the carrier device 2. The sensor carrier 3 is arranged such that it is rotatable around the pipes to be welded or the welded pipes or the weld seam, preferably by 360°, therefore around the entire pipe. This is achieved with the embodiment illustrated in FIG. 1 in that the sensor carrier 3 is driven by the two drives 8, which preferably run synchronously, and during the rotation of the sensor carrier 3 around the centre axis thereof or around the pipeline axis, at least one drive 8 is engaged in each case with the sensor carrier 3, because of which the drives 8 and the sensor carrier 3 preferably have gear teeth (not shown), wherein the sensor carrier 3 can also be driven in other ways.

Figure 2:
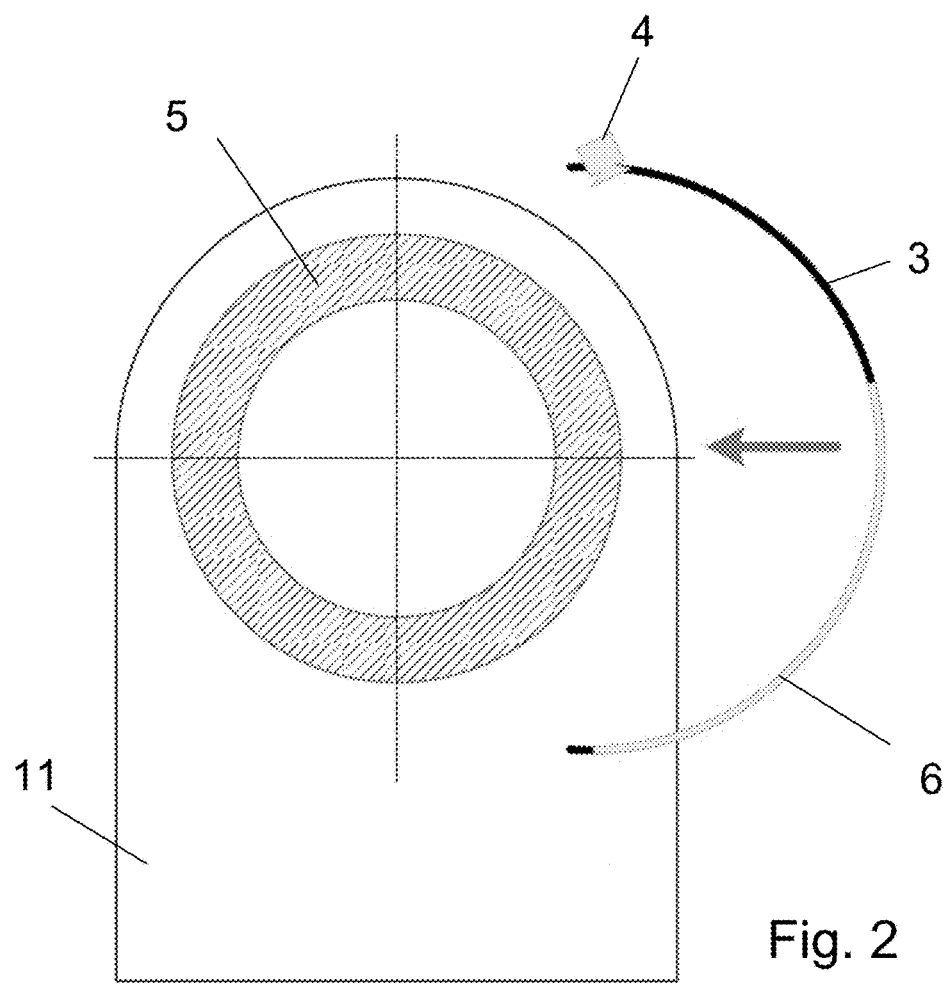
FIG. 2 shows a schematic view of a device according to an embodiment of the invention, wherein only the sensor carrier without carrier device is shown.

The sensor carrier 3 preferably has a C shape. In addition to the advantage of good rotation capability, this also provides the advantage that the sensor carrier 3 can be moved easily over the pipe ends to be welded or over the already welded pipes, as is recognizable in FIG. 2, and is subsequently arranged concentrically in relation to the pipe 5, whereby the circling of the sensor carrier 3 having the sensor 4 arranged thereon is implementable easily to enable an examination of the entire weld seam. The C shape is implemented such that it is possible for the sensor carrier 3 to travel over the pipe even in the case of the largest pipe diameter to be examined on the corresponding device 1.

An electronic light-sensitive sensor 4 is arranged on the sensor carrier 3. Such sensors 4 are known as CCD sensors or also as CMOS sensors from the prior art, wherein such sensors 4 are found in digital cameras and instead of a sensor 4, which is combined with an optics system, a digital camera can also be used, which contains such a sensor 4. It is important for the installation of such a sensor 4 with an optics system required for this purpose, or the digital camera, that the sensor with the optics system or the digital camera is constructed compactly. The space conditions for the device 1 according to an embodiment of the invention are recognizable in FIG. 3. The device 1 according to an embodiment of the invention must be insertable between the pipe clamps 10 and this requires a narrow sensor 4 and also the carrier device 2 and the sensor carrier 3 must be designed as very thin, since these also still protrude between the pipe clamps 10 and the pipe clamps 10 are moved together relatively close due to the welding procedure. In addition, the device 1 according to an embodiment of the invention has an illumination unit 6, so that the weld seam or weld bead recorded by the sensor 4 is clearly recognizable and the contour stands out clearly. In FIG. 1, the illumination unit 6 is disclosed as a backlight 6, wherein the backlight 6 is implemented as a light screen 6 in FIG. 1. Therefore, all dimensions of pipe diameters which can be examined on the device 1 are ideally illuminated by the backlight 6. In FIG. 1, the dashed line represents the theoretical smallest pipe diameter, wherein the centre of the pipes 5 was used as a representative of the smallest diameter here. It is therefore recognizable from FIG. 1 that the capture of the weld seam by means of the sensor 4 and the corresponding illumination by the backlight 6 is possible from a minimal pipe diameter up to a maximal pipe diameter, which is shown here, without having to perform a change on the device 1, wherein the sensor 4 or the digital camera 4 and/or the mirror 7 can be arranged so they are movable or moving on the sensor carrier 3, on the one hand, to expand the range of the pipe diameters which can be captured and, on the other hand, to be able to perform a fine adjustment for an optimum recording. Furthermore, it is advantageous if the device 1 has a mirror 7, since it enlarges the optical path from the sensor 4 to the weld seam, as is apparent in FIG. 1.

Figure 4:
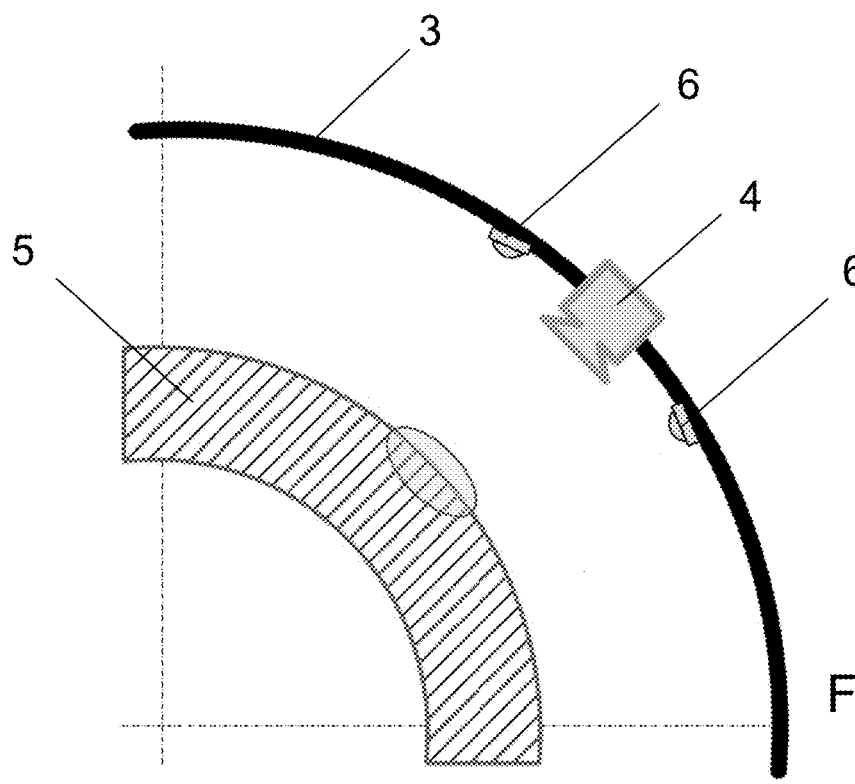
FIG. 4 shows a schematic illustration of a device according to an embodiment of the invention, wherein the illumination unit is arranged as an incident light.

FIG. 4 shows the illumination unit 6 embodied as an incident light. The incident light illuminates the weld seam at the position of the recording, wherein the recording of the weld seam by the sensor 4 or the digital camera is performed vertically on the weld seam or the circumference of the pipes 5. By way of this type of the recording, primarily contaminants and irritations on the surface are recognized and/or the pipe or fitting material is identified.

Figure 5:
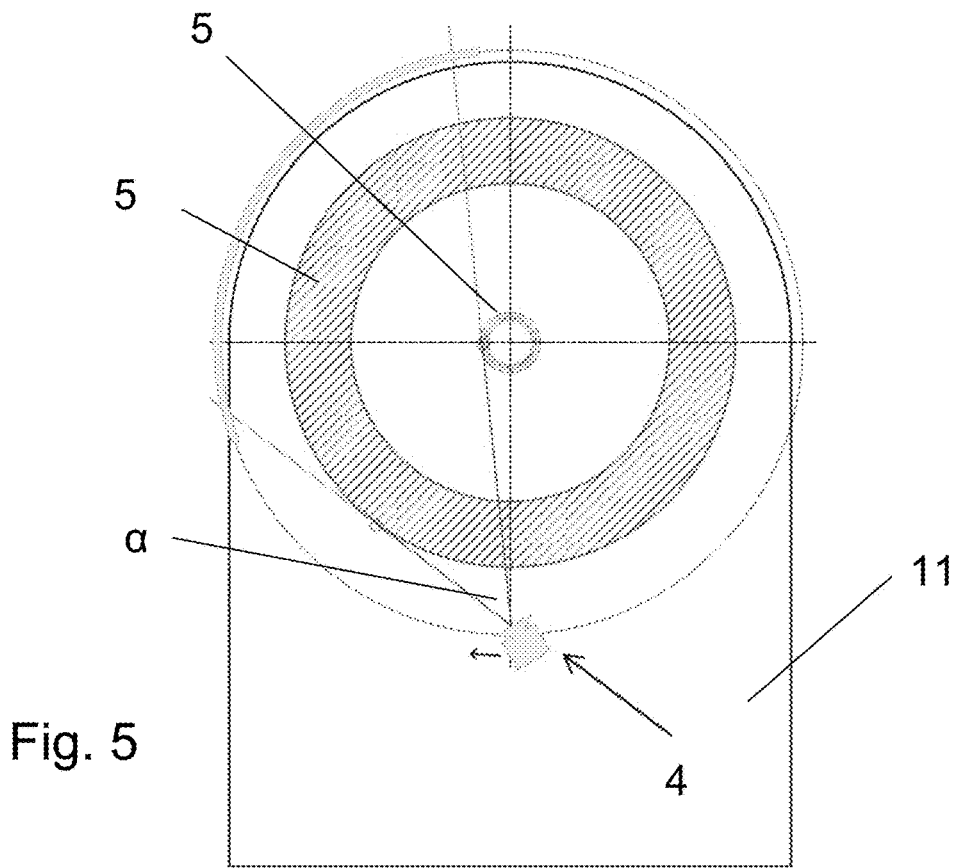
FIG. 5 shows a schematic illustration of a device according to an embodiment of the invention, wherein the illumination unit is arranged as a backlight.

FIG. 5 shows the schematic illustration in the case of the use of backlight 6. The contour of the weld seam or weld bead stands out clearly due to the use of the backlight 6. In the case of the use of backlight 6, the sensor 4 must be oriented tangentially to the pipe diameter or to the weld seam. The backlight 6 accordingly emits in the opposite direction. Of course, both the embodiment of the backlight and incident light can be fastened on the sensor carrier 3 to carry out the different examinations, and the possibility also exists of the sole use of backlight or incident light. In FIG. 5, the smallest and the largest pipe diameters are each shown, for which the device 1 is applicable. The sensor 4 therefore has a correspondingly large viewing angle α, to cover the largest possible range of the possible pipe diameters, which can be examined using the device 1. Since the position of the backlight 6 also changes according to the pipe diameter, and this backlight is also fixedly arranged on the sensor carrier 3, however, the backlight 6 is formed by a light screen 6, which extends concentrically in relation to the pipe circumference or along the inner surface of the C shape of the sensor carrier 3. A corresponding light screen 6 can be recognized well in FIG. 1. Concatenated LEDs can be used as possible luminaries, wherein other luminaries are also conceivable.

Figure 6:
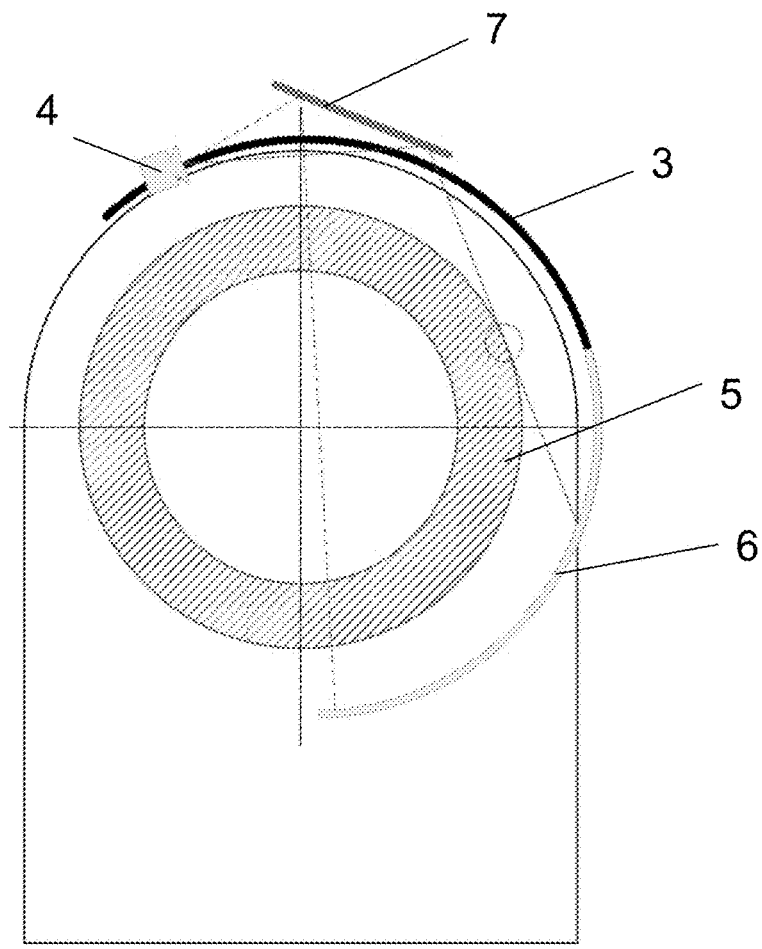
FIG. 6 shows a schematic illustration of a device according to an embodiment of the invention, having backlight and mirror.
Figure 7:
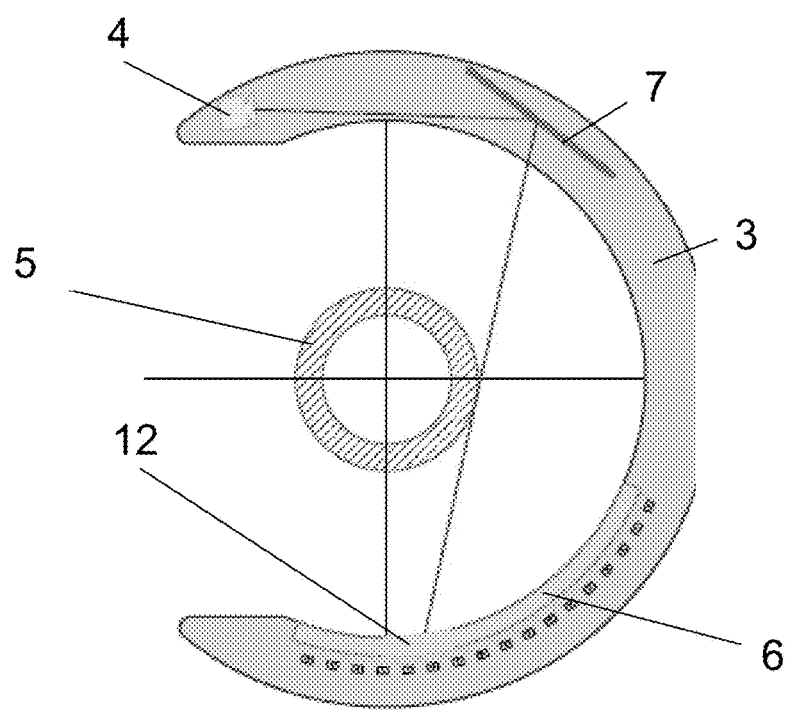
FIG. 7 shows a schematic illustration of a device according to an embodiment of the invention, having light screen, wherein the light screen is only regionally illuminated.

FIG. 7 illustrates the regional turning on and off of the light screen 6, wherein the embodiment of the device according to an embodiment of the invention shown in FIG. 7 still has a mirror 7 and the sensor 4 executes the recording of the weld seam indirectly via the mirror 7. The backlight 6 also emits in the opposite direction here, however, wherein only an illuminated region 12 of the backlight 6 is turned on, whereby a reflection of the illumination unit vertically in relation to the weld seam can be avoided and thus the recordings are not interfered with and are more clearly recognizable. It must always be taken into consideration in this case that the sensor carrier 3 rotates 360° around the weld seam or the pipe ends, while the sensor 4 makes the recordings. FIG. 6 once again illustrates the advantage of a mirror 7. As already mentioned, the recording is performed tangentially by the sensor 4 using backlight 6. In order that the entire width of the weld seam or the weld bead is illuminated or encompassed by the backlight 6, it is advantageous if the distance from the sensor 4 to the recording point of the weld seam is relatively large, which enlarges the perceived width of the backlight 6 and enables the complete coverage of the weld seam width by means of the backlight 6, whereby the contour of the weld seam or weld bead stands out clearly, this is also well recognizable in the illustrations from FIG. 9.

The enlargement of the distance between the sensor and the weld seam also causes the path difference (optical path) between the largest and smallest pipe dimensions, considered relatively, to become smaller. An adjustment of the depth of field can thus be omitted. The image remains sharp and clearly recognizable in the case of every dimension.

The variants of the possible minimal and maximal pipe diameters are also shown in FIG. 6, although the smallest diameter is only indicated by means of a dashed tangent drawn on the imaginary smallest diameter, wherein an expansion of the range which can be captured is also possible here by way of a movable sensor and/or mirror, as in FIG. 7.

Figure 8:
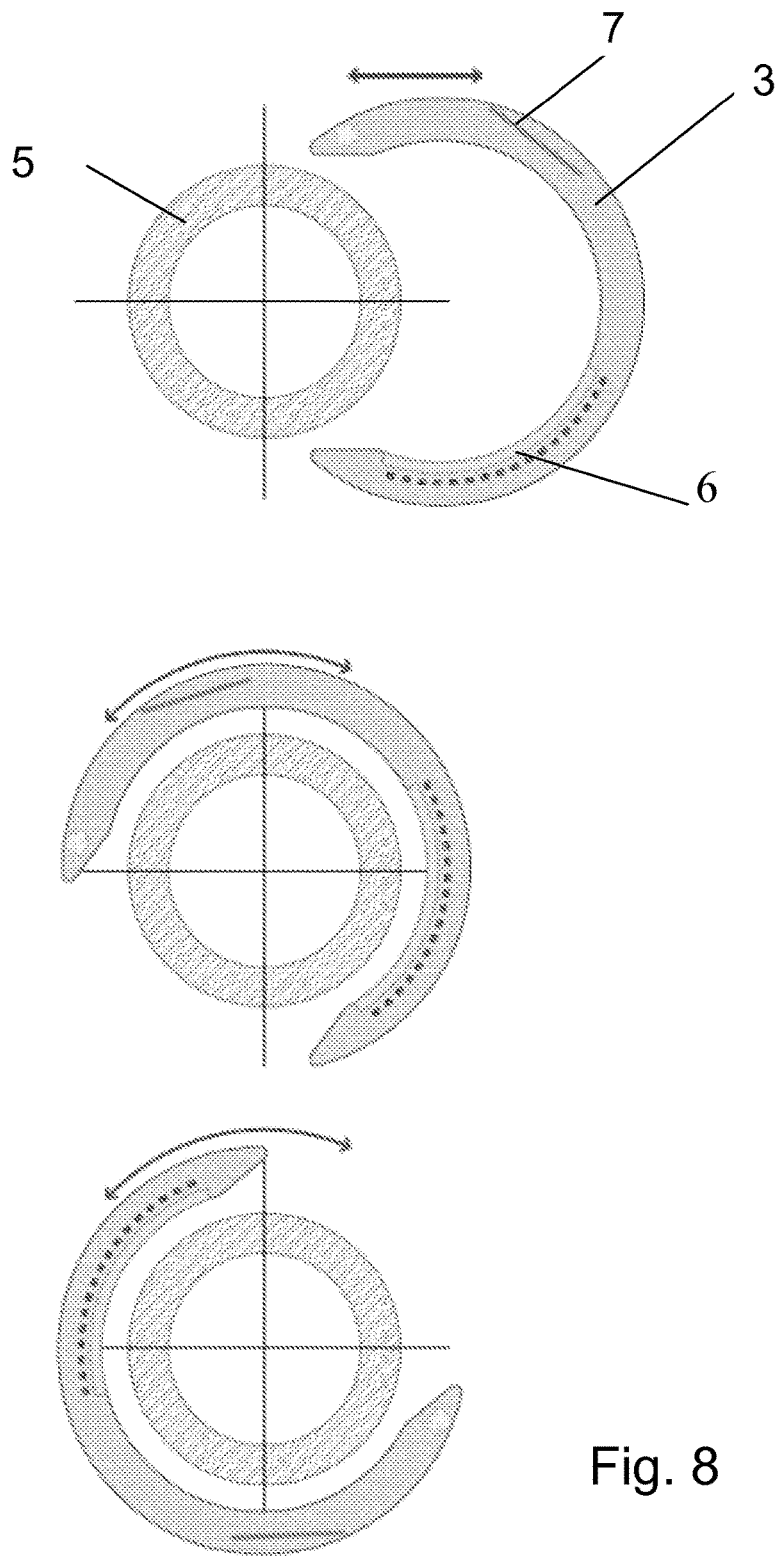
FIG. 8 shows a schematic illustration of the movement sequence of the sensor carrier.

FIG. 8 illustrates the sequence for the arrangement around the pipes and the examination thereof of the sensor carrier 3. At the beginning, the sensor carrier 3 is moved over the pipes 5, which is enabled by the C shape of the sensor carrier 3. Furthermore, it is shown that the sensor carrier 3 with the sensor 4 arranged thereon, the mirror 7, and the illumination unit 6, which is implemented here as a backlight 6, may be rotated around the pipe 5, preferably by 360°, so that the weld seam or the pipe ends can be examined completely.

Figure 9:
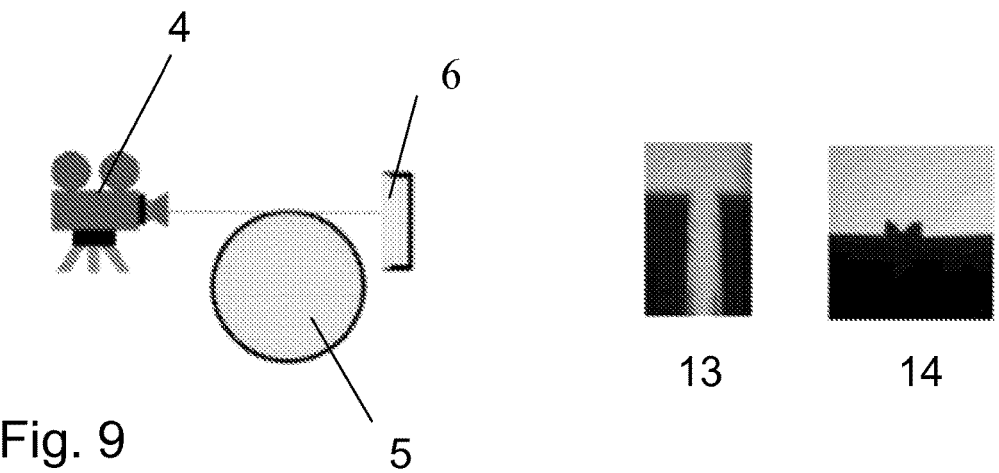
FIG. 9 shows a schematic arrangement of the sensor, the pipe, and the illumination unit with the captured recordings by the sensor.

FIG. 9 illustrates a schematic examination according to an embodiment of the invention of the pipe ends before the welding and an examination after the welding by the examination of the weld seam. The sensor 4 is oriented tangentially onto the pipe diameter of the pipe ends 5 to be welded or the weld seam thereof after the welding and is tangentially irradiated by backlight 6. The sensor 4 captures the recordings 13, 14. The recording 13 represents the two pipe ends 5 before the welding and enables by way of the recording of the sensor 4, which can be performed continuously or as individual recordings, the capture of the diameter, the ovality, the mutual offset, the surface composition, etc. The weld seam can be captured similarly, which is represented in the recording 14. In this case, the geometry of the weld seam 9 or the weld bead 9, the shape, the size, the area, and possible irritations and contaminants can also be ascertained by the recording.

Figure 10:
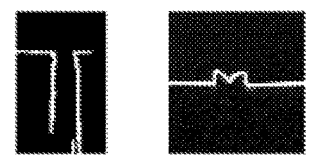
FIG. 10 shows the converted recording into the contour only to enable the comparison.

These captured data are then converted by the controller such that only the contour is still imaged as in FIG. 10, processed further, or used for data comparison. These ascertained contours can subsequently be compared to the standards and/or comparison values or boundary conditions stored in the controller and result in the reliability or the non-reliability of a weld seam or the pipe ends, in that it is judged on the basis of the ascertained properties and dimensions thereof whether the corresponding weld seam meets or does not meet the requirements. The captured data can also be stored for documentation purposes.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE SIGNS 1 device for contactless examination of a butt weld
2 carrier device
3 sensor carrier
4 sensor, electronic light-sensitive sensor, digital camera
5 pipe, pipe ends or fitting, fitting ends
6 illumination unit/light screen/backlight/incident light
7 mirror
8 drive
9 weld seam
10 pipe clamp or fitting clamp
11 butt weld seam
12 illuminated region of the light screen
13 pipe end recording by sensor before welding
14 weld seam recording by sensor
α viewing angle of sensor

What is claimed is:

1. A device for contactless examination of a butt weld of plastic pipes and fittings, the device comprising:
   a carrier device,
   an illumination unit,
   a sensor carrier, and
   at least one electronic light-sensitive sensor for optically monitoring pipe ends or fitting ends to be welded and the weld seam,
   wherein the sensor carrier is arranged on the carrier device in a movable or rotatable manner such that the sensor carrier is rotatable about the pipe ends or fitting ends to be welded and/or the weld seam, and
   wherein the electronic light-sensitive sensor is arranged on the sensor carrier.

2. The device according to claim 1, wherein the sensor carrier is rotatable by 360° around the pipe ends or fitting ends to be welded and/or around the weld seam.

3. The device according to claim 1, wherein the sensor carrier is C shaped.

4. The device according to claim 1, wherein the at least one sensor is oriented tangentially or indirectly tangentially on a circumference of the pipe ends or fitting ends to be welded and/or the weld seam.

5. The device according to claim 1, wherein the illumination unit is arranged as a backlight.

6. The device according to claim 1, further comprising a mirror arranged on the sensor carrier.

7. The device according to claim 1, wherein the illumination unit is arranged as an incident light, and
   wherein the sensor is oriented perpendicularly or approximately perpendicularly to the position to be recorded.

8. The device according to claim 1, wherein the device is arranged on a butt welding machine or is implemented as an autonomous module adaptable for being retrofitting on a butt welding machine.

9. The device according to claim 1, wherein the illumination unit is arranged on the sensor carrier.

10. The device according to claim 1, further comprising a mirror arranged on the sensor carrier, wherein the at least one electronic light sensitive sensor is oriented tangentially or indirectly tangentially onto the circumference of the weld seam via the mirror.

11. A method for contactless examination of a butt weld of plastic pipes and fittings, the method comprising:
    chucking or fixing pipe ends to be welded at opposing end sides;
    planing the pipe ends to be welded;
    carrying out an optical contactless examination of the pipe ends to be welded with an electronic light-sensitive sensor and an illumination unit;
    butt welding the pipe ends;
    carrying out an optical contactless examination of a weld seam with the electronic light-sensitive sensor and the illumination unit during a cooling operation,
    wherein the electronic light-sensitive sensor is arranged on a carrier sensor,
    wherein the sensor carrier is arranged on a carrier device in a movable or rotatable manner such that the sensor carrier is rotatable about the pipe ends to be welded and/or the weld seam, and
    wherein carrying out the contactless examination of the weld seam includes rotating the electronic light-sensitive sensor by 360° around the pipe ends to be welded or around the weld seam for the contactless examination.

12. The method according to claim 11, wherein the illumination unit includes one of a backlight or an incident light for illuminating the pipe ends to be welded or the weld seam.

13. The method according to claim 11, wherein the illumination unit is arranged on the sensor carrier.

* * * * *